United States Patent [19]

Breslow et al.

[11] Patent Number: 4,920,216

[45] Date of Patent: Apr. 24, 1990

[54] SELECTIVE CHLORINATION OF STEROIDS AND OTHER SUBSTRATES DIRECTED BY COVALENTLY LINKED PYRIDINE DERIVATIVES ACTING AS TEMPLATES

[75] Inventors: Ronald Breslow, Englewood, N.J.; Michael Brandl, New York, N.Y.; Alan D. Adams, New York, N.Y.; Jurgen Hunger, New York, N.Y.

[73] Assignee: The Trustees of Columbia in the City of New York, New York, N.Y.

[21] Appl. No.: 55,139

[22] Filed: May 28, 1987

[51] Int. Cl.$^5$ ............................ C07J 43/00; C07J 1/00
[52] U.S. Cl. .................................. 540/110; 552/595; 552/544; 552/574; 552/576; 552/566
[58] Field of Search ....................... 260/397.47, 397.5; 540/110

[56] References Cited

PUBLICATIONS

Journal of the American Chemical Society, vol. 109 No. 12; pp. 3799–3801; Jun. 10, 1987; Breslow et al.

*Primary Examiner*—Joseph A. Lipovsky
*Attorney, Agent, or Firm*—John P. White

[57] ABSTRACT

This invention concerns a method of substituting a chlorine atom for a predetermined hydrogen atom located within an organic compound which comprises contacting the organic compound containing the predetermined hydrogen atom with an esterifying agent comprising a pyridine ring or a substituted or fused ring derivative of a pyridine ring so as to produce an ester and treating the ester with a chlorinating agent so as to substitute the chlorine atom for the predetermined hydrogen atom. The ester comprises the pyridine ring or the substituted or fused ring derivative of the pyridine ring so positioned within the ester with respect to the predetermined hydrogen atom that a chlorine atom attached to the nitrogen atom of the pyridine ring or substituted or fused ring derivative of the pyridine ring reacts with the predetermined hydrogen atom.

Another aspect of the invention is a method for converting a predetermined single bond between a carbon atom and another atom in an organic compound into a double bond between the carbon atom and the other atom which comprises substituting a chlorine atom for a predetermined hydrogen atom bound to the carbon atom or the other atom of the organic compound according to the method of this invention so as to produce a chlorine-containing compound and then treating the chlorine-containing compound so as to eliminate the chlorine atom from the compound and form the double bond.

24 Claims, No Drawings

SELECTIVE CHLORINATION OF STEROIDS AND OTHER SUBSTRATES DIRECTED BY COVALENTLY LINKED PYRIDINE DERIVATIVES ACTING AS TEMPLATES

The invention described herein was made in the course of work under Grant No. CHE-83-00253 from the National Science Foundation. The U.S. Government has certain rights in this invention.

BACKGROUND OF THE INVENTION

Throughout this application various publications are referenced and citations are provided in parentheses for them. The disclosures of these publications in their entireties are hereby incorporated by reference into this application in order to more fully describe the state of the art to which this invention pertains.

Steroids, particularly 5-alpha-steroids and 4,5 dehydro analogs thereof, are well known chemical compounds which exhibit significant physiological activity. Steroids having a keto group at the 3-position are especially important in this regard. 5-alpha-steroids of the androstane series are presently utilized as anabolic agents and fertility control drugs and as intermediates in the preparation of such agents and drugs. Certain steroids of the pregnane series are particularly effective as anti-inflammatory agents and as cardenolides. Steroids of the cholestane series, such as cholesterol and sitosterols, particularly beta-sitosterol, are naturally occurring compounds and are already useful or are potentially useful as starting materials for te commercial preparation of therapeutically important steroids.

Steroids which include a wide variety of substituent groups are useful therapeutically. For example, 9-alpha-fluoro substituted steroids and 16-alpha-methyl substituted steroids, such as 9-alpha-fluoroprednisolone, triamcinolone, 16-alpha-methylprednisolone, and dexamethasone, exhibit high glucocorticoid and anti-inflammatory activity. (U.S. Pat. Nos. 2,864,836 [1958] and 2,838,547 [1958]; and generally L. F. Fieser and M. Fieser, STEROIDS, Van Nostrand Reinhold Co. [1959], pp. 682–696). In the androstane series, 11-beta-hydroxyl substituted compounds which have antiandrogenic and gonadotropic activity have been described (U.S. Pat. Nos. 2,732,479 [1956] and 2,702,811 [1955]). Those skilled in the art to which this invention pertains will know other compounds characterized by the basic sterioid nucleus which may be utilized either directly as, or indirectly to provide, useful compounds.

Synthetic procedures are known for the production of useful steroids from naturally occurring steroids. Diosgenin is an important source of steroids of the pregnane series such as prednisolone and its numerous derivatives. Because of their ready availability from plant sources, sitosterols, particularly beta-sitosterol, have been often studied as commercially useful starting materials for the synthesis of 5-alpha-steroids of the pregnane and androstane series. However such approaches have not met with significant success, principally because of difficulties in removing the side chain, except in low yield, and in introducing functional groups into a molecule devoid of such groups other than the 3-beta-hydroxy group and the double bond at the 5,6 position.

Available methods for removing the side chain include chemical and microbiological oxidation. Unfortunately, the yields from these procedures are unacceptably low. Moverover, a significant capital investment is required to construct, operate and maintain a plant to carry out microbiological oxidation.

Methods have previously been developed to direct chlorination to various tertiary positions on steroids by the use of attached iodine— or sulfur— containing templates. The resulting chlorinated steroids may then be used as precusors to introduce double bonds or other functional groups at the chlorinated site. (Breslow, R., Corcoran, R. J., and Snider, B. B., J. Am. Chem. Soc. 1974, 96: 6791; Breslow, R., Corcoran, R. J., Snider, B. B., Doll, R. J., Khanna, P. L. and Kaleya, R., J. Am. Chem. Soc. 1977, 99: 905; Breslow, R., Wife, R. L. and Prezant, D., Tetrahedron Letters 1976, 23: 1925; and Breslow, R. and Heyer, D., J. Am. Chem. Soc. 1982, 104: 2045).

In Breslow et al., U.S. Pat. No. 4,252,719 (1981), a method for the selective removal of tertiary hydrogen atoms on steroid nuclei and side chains is described. This method requires that the steroid be esterified by iodo aryl substituted acids, acid anhydrides, or acid chlorides, thereby covalently binding a iodo aryl template compound being covalently bound to the steroid. Breslow et al., U.S. Pat. No. 4,323,512 (1982), discloses an improvement on this method so as to directly esterify the 17-alpha-hydroxy group of a steroid to form the covalently bound iodo aryl template compound.

Once the template is attached, the steroid esters is then chlorinated under free radical generating conditions in order to selectively replace the hydrogen with a chlorine. The chlorinated steroid ester is thereafter dehydrochlorinated to produce the unsaturated steroid.

An iodo aryl template which halogenates three steroid substrates has also been described. Breslow, R. and Heyer, D., J. Am. Chem. Soc. 1982, 104: 2045.

The present invention provides a method for substituting a chlorine atom for a hydrogen atom on a steroid nucleus by using a template compound comprising a pyridine ring or a substituted or fused ring derivative thereof. The template compound of the present invention possesses several advantages over the above-described templates containing an iodaryl or sulfur aryl group. For example, nicotinic acid, which may be used as a starting material for the template compound, is part of the natural vitamin niacin, and therefore, harmless if ingested as a contaminate in the end-resulting medicinal products. Moreover, the geometry of the chlorine atom adduct of a pyridine compound is expected to be different than the geometry of the chlorine atom adduct of iodo aryl compounds. Therefore, selectivities of the two adducts are expected to be different. Pyridine compounds are also basic, while the iodo and sulfur-containing templates are not. Thus, pyridine templates may be removed and recovered by extraction with acid, while the previously known templates cannot. Additionally, pyridine derivatives are generally more available than are iodobenzene derivatives, thereby making pyridine-containing templates more economical.

SUMMARY OF THE INVENTION

This invention concerns a method of substituting a chlorine atom for a predetermined hydrogen atom located within an organic compound which comprises contacting the organic compound containing the predetermined hydrogen atom with an esterifying agent comprising a pyridine ring or a substituted or fused ring derivative of a pyridine ring so as to produce an ester and treating the ester with a chlorinating agent so as to substitute the chlorine atom for the predetermined hydrogen atom. The ester comprises the pyridine ring or the substituted or fused ring derivative of the pyridine ring so positioned within the ester with respect to the predetermined hydrogen atom that a chlorine atom attached to the nitrogen atom of the pyridine ring or substituted or fused ring derivative of the pyridine ring reacts with the predetermined hydrogen atom.

Another aspect of the invention is a method for converting a predetermined single bond between a carbon atom and another atom in an organic compound into a double bond between the carbon atom and the other atom which comprises substituting a chlorine atom for a predetermined hydrogen atom bound to the carbon atom or the other atom of the organic compound according to the method of this invention so as to produce a chlorine-containing compound and then treating the chlorine-containing compound so as to eliminate the chlorine atom from the compound and form the double bond.

The invention also provides a method for producing a compound in the betamethasone, dexamethasone, triamcinolone or prodnisolone family which comprises converting a predetermined single bond between carbon-9 and carbon-11 in a steroid into a double bond by the method of this invention.

The invention further concerns a compound having the structure:

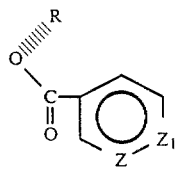

wherein R is a steroid of the cholestane, androstane or pregnane series and either Z or $Z_1$ is a nitrogen atom and the other is a carbon atom.

DETAILED DESCRIPTION OF THE INVENTION

This invention concerns a method of substituting a chlorine atom for a predetermined hydrogen atom located within an organic compound which comprises contacting the organic compound containing the predetermined hydrogen atom with an esterifying agent comprising a pyridine ring or a substituted or fused ring derivative of a pyridine ring so as to produce an ester and treating the ester with a chlorinating agent so as to substitute a chlorine atom for the predetermined hydrogen atom. The ester comprises the pyridine ring or the substituted or fused ring derivative of the pyridine ring so positioned within the ester with respect to the predetermined hydrogen atom that a chlorine atom attached to the nitrogen atom of the pyridine ring or the substituted or fused ring derivative of the pyridine ring reacts with the predetermined hydrogen atom.

Essentially any organic compound may be used in the practice of the subject invention. Merely by way of example suitable organic compounds include aromatic compounds, including benzyl, naphthyl, anthryl, and steryl compounds, and aliphatic compounds, including alkyl, alkenyl and alkynyl compounds. Presently, the preferred organic compound is one which contains between about 10 carbon atoms and 50 carbon atoms. In accordance with the presently preferred embodiments of the invention, the organic compound is a steroid, particularly a steroid of the pregnane, androstane, or cholestane series comprising a hydroxyl group. In the most preferred embodiments, the steroid is a cholestane steroid comprising a 3-alpha-hydroxy group, a pregnane steroid comprising a 17-alpha-hydroxyl group, or a cortexolone steroid. The steroid may also comprise a methyl group at carbon-3 or carbon-16 in the alpha or beta position, preferably at carbon-16 in the alpha position.

Although the method is suitable for substituting a chlorine atom for any predetermined hydrogen atom on the organic compound, the method is particularly useful for a predetermined hydrogen atom attached to a steroid at carbon-6, -9, -14, -17 or -20 position, especially a hydrogen atom at carbon-9 or carbon-14 position.

In the practice of this invention, suitable esterifying agents include compounds comprising a nitrogen-containing ring such as a pyridine, oxazole, thiazole, imidazole, pyrazole, isoxale, pyrimidine or quinoline ring or a substituted or fused ring derivative thereof. Particularly useful esterifying agents are pyridine-derived carboxylic acids, such as acids comprising a nicotinate or isonicotinate moiety.

The contacting of the organic compound and the esterifying agent may be effected in the presence of an organic solvent, such as dimethoxyethane, to form a mixture. Contacting may also comprise heating, quenching or extracting the mixture. In the preferred embodiments, the contacting is effected in dimethoxyethane and the mixture is heated, quenched in ammonium chloride, and extracted with methylene chloride.

In certain embodiments of the invention, the organic compound is a steroid which is contacted with the esterifying agent so as to produce the ester at the 3-alpha, 5-alpha, 6-beta, 7-alpha or 17-alpha position of the steroid. Presently an ester produced at the 3-alpha or 17-alpha position of the steroid is preferred.

In preferred embodiments of the invention the ester is a nicotinic acid steroid ester or a isonicotinic acid steroid ester or a derivative thereof. Especially preferred steroid esters are 3-alpha-cholestanyl nicotinate, 3-alpha-cholestanyl isonicotinate, 17-alpha-cortexolone nicotinate, 17 alpha-cortexolone isonicotinate, 16-alpha-methylcortexolone-17-alpha-nicotinate, or 16-alpha-methylcortexolone-17-alpha-isonicotinate.

Suitable chlorinating agents includes those capable of substituting a chlorine atom for a hydrogen atom. Preferably, the chlorinating agent is selected from the group consisting of molecular chlorine, phenyliodinedichloride or sulfuryl chloride, particularly useful is phenyliodinedichloride.

The treating of the ester typically is effected in solutions containing the ester and the chlorinating agent and an organic solvent, such as methylene chloride ($CH_2Cl_2$) or methylene chloride/acetonitrile ($CH_2Cl_2/CH_3CN$). In certain embodiments, treating further comprises degassing the solution with an inert gas such as Argon or separating the organic compound with the chlorine atom substituted for the predetermined hydrogen atom by column chromatography or crystallization. In other embodiments, treating further comprises irradiating the solution or contacting the solution with a scavenger to neutralize the removed hydrogen atom, e.g. contacting with potassium acetate (KOAc), epoxybutane, or aqueous sodium bicarbonate ($NaHCO_3$) to neutralize hydrogen chloride (HCl).

Another aspect of the invention is a method for converting a predetermined single bond between a carbon atom and another atom in an organic compound into a double bond between the carbon atom and the other atom which comprises substituting a chlorine atom for a predetermined hydrogen atom bound to the carbon atom or the other atom of the organic compound according to the method of this invention so as to produce a chlorine-containing compound and then treating the chlorine-containing compound so as to eliminate the chlorine atom from the compound and form the double bond.

Treating is typically effected by dehydrochlorination, preferably with KOH, AgBF$_4$ or AgNO$_3$ in an organic solvent. In the preferred embodiments, the other atom is a carbon atom and the organic compound is a steroid of the cholestane, androstane or pregnane series and the predetermined single bond is between carbon-9 and carbon-11 in the steroid.

The invention also provides a method for producing a compound in the betamethasone, dexamethasone, triamcinolone or prodnisolone family which comprises converting a predetermined single bond between carbon-9 and carbon-11 in a steroid into a double bond by the method of this invention.

The invention also concerns a compound having the structure:

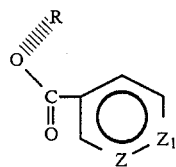

wherein R is a steroid moiety of the cholestane, androstane or pregnane series and either Z or $Z_1$ is a nitrogen atom and the other is a carbon atom. In certain embodiments, the compound also comprises a chlorine atom attached to the nitrogen atom of the pyridine ring. Preferably, the group having the structure:

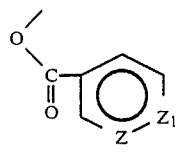

is attached to the steroid moiety at the 3-alpha or 17-alpha position and the steroid moiety is a cholesterol, cortexolone, or methylcortexolone moiety. Especially preferred are compounds having the structures:

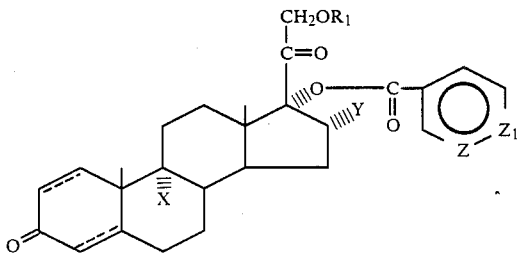

wherein Z and $Z_1$ are the same as defined previously; X is a hydrogen or chlorine atom; Y is a hydrogen atom or a methyl group; $R_1$ is a hydrogen atom or an acetate group; and the dotted lines (....) represent bonds which may be present or absent.

In the most preferred embodiments, the compounds have the structure:

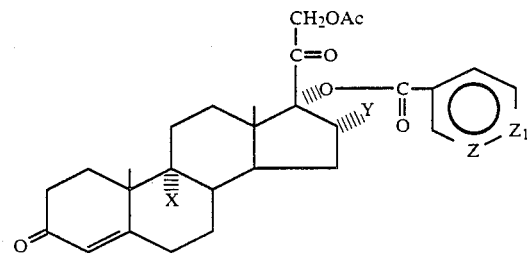

wherein Z, $Z_1$, X and Y are the same as defined previously.

Certain embodiments of this invention are exemplified in the Examples which follow. The Examples are set forth to aid in the understanding of the invention but are not intended to, and should not be construed to, limit in any way the invention as set forth in the claims which follow thereafter.

EXAMPLE 1

On 15 min. irradiation with 1.2 eqiuv. phenyliodinedichloride (PhICl$_2$) and 6 equiv. 1,2-epoxybutane, under conditions previously described (Maitra, U., Breslow, R., Tetrahedron Letters, 1986, 27: 3087-90), 3-alpha-cholestanyl nicotinate (1) at 20 mM was quantitatively chlorinated to the 9-chloro derivative 2, contaminated by the 14-chloro derivative 3. The mixture was analyzed by hydrolysis/dehydrochlorination with KOH to form the 9(11) olefin (92% isolated yield) and the Δ14 olefin (3% yield), respectively. With the isonicotinate ester 4 the changed geometry led to 44% recovered starting material, 37% 9(11) olefin, 14% Δ14 olefin, and 5% of a product formed by double chlorination.

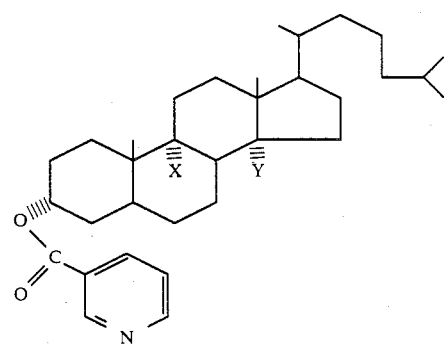

1  X = Y = H
2  X = Cl, Y = H
3  X = H, Y = Cl

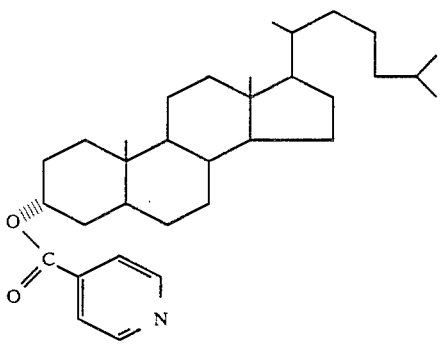

4

EXAMPLE 2

Irradiation of 6 (3 mM) with 1.5 equiv. $PhICl_2$ and 5 equiv. finely powdered $K_2CO_3$ in $CH_2Cl_2$ for 30 min. produced the 9-chloro derivative 8 in greater than 98% yield. This was dehydrochlorinated to the 9(11) olefin with $AgBF_4$ in acetone, and the product was converted by hydrolysis ($K_2CO_3$ in MeOH) and reacetylation to the 21-acetate 9 whose NMR spectrum was identical with the published NMR spectrum (Zomer, B., Wynberg, H., Drayer, N.M., Steroids 1984, 44: 293–300). In a similar fashion the corresponding 16-alpha-methyl steroid 7 was converted to the chloro derivative 10 and the 9(11) olefin 11 which was identical with an authentic sample. When the reaction of 6 was performed at a higher concentration (21 mM) a side reaction resulting in allylic chlorination competed with the template-directed process and led to a 1:2 ratio of carbon-6 to carbon-9 chlorosteroid.

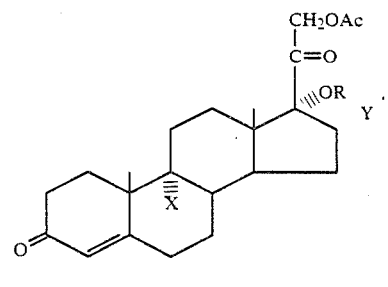

6  X = Y = H; R = 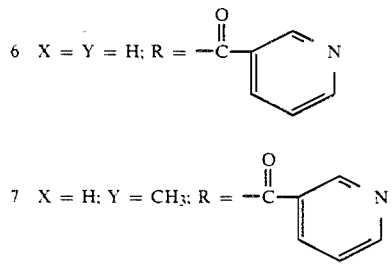

7  X = H; Y = $CH_3$; R =

8  X = Cl; Y = H; R = 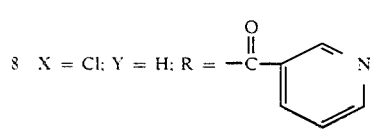

10  X = Cl; Y = $CH_3$; R =

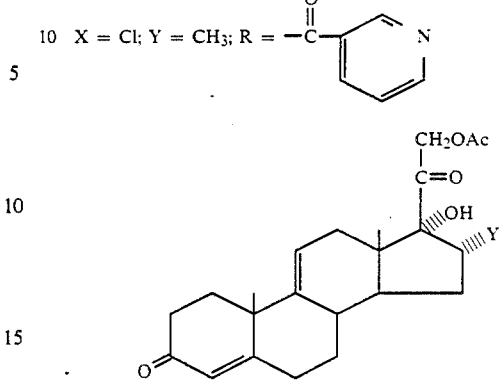

9  Y = H
11  Y = $CH_3$

EXAMPLE 3

To a 17 mM solution of 3-alpha-cholestanyl isonicotinate in $CH_2Cl_2/CH_3CN$ (in a 14:1 volume ratio) were added 1.14 equivalents of freshly recrystallized phenyliodinedichloride and 5 equivalents potassium acetate (undissolved). The mixture was degassed with Argon, irradiated for 10 min. at 0° C. with a 275 W sunlamp from 20 cm distance, then quenched with an excess of 10%(w/v) aqueous $NaHSO_3$ solution and washed with water and then brine. The solvent was removed, an excess of 6%(w/v)KOH in $CH_3OH$/dioxane/$H_2O$ (15/4/1(v/v/v)) was added and this mixture was refluxed for 2 hours. The solvent was removed in vacuo, the residue taken up in ether/water, the organic layer washed with water and neutralized with very dilute HCl-solution and $NaHCO_3$ solution. After drying over $Na_2SO_4$ the solvent was removed in vacuo. NMR in $CHCl_3$ showed the following product distribution: 44% recovered 3-alpha-cholestanol, 37% $\Delta9(11)$-3-alpha-cholestenol, and 14% $\Delta14$-3-alpha-cholestenol.

EXAMPLE 4

200 mg of 3-alpha-cholestanyl nicotinate (0.4 mmoles) and 130 mg of iodobenzenedichloride were dissolved in 19 ml of dichloromethane. 200 ml of epoxybutane (2.3 mmoles) was added as a hydrogen chloride scavenger and the solution was irradiated with a sunlamp for 10 minutes.

9-chloro-3-alpha cholestanyl nicotinate was isolated by evaporating the solvent and was purified on a silica column. Without purification 9-chloro-3-alpha-cholestanyl nicotinate was converted to $\Delta9(11)$-3-alpha-cholestenol by refluxing in a solution of 5 ml of 6% potassium hydroxide in methanol:dioxane:water (600:160:40 volume ratio) for 90 minutes. The solvent was removed by evaporation and 145 mg of steroidal products were isolated by extraction with diethylether. The mixture consisted of 95% $\Delta9(11)$-3-alpha-cholestenol, 3% $\Delta14$-3-alpha-cholestenol and less than 1.5% 3-alpha-cholestanol.

EXAMPLE 5

The 17-nicotinate 12 (100 mg, 0.21 mmole, 1.0 equiv.) was dissolved in 70 ml dry $CH_2Cl_2$. Finely powdered $K_2CO_3$(146 mg., 1.1 mmol., 5.0 equiv.) was added. Phenyl-iodine dichloride (87mg. 0.32 mmol. 1.5 eg.) was added as a solid. The mixture was irradiated with a 275

W sunlamp at a distance of 15 cm. The solution was maintained at 25° C. with a water bath.

At ½ hr, the above solution was poured into ½ volume 10% NaHSO₃(aq). The aqueous phase was extracted four times with equal volume of CH₂Cl₂. The combined extracts were dried over Na₂SO₄, filtered, and reduced in vacuo.

The crude 9-alpha-chloride 13 was treated with AgBF as described in Example 6. The crude product was greater than 97% pure. A trace of the 6-chloro compound was detectable.

lamp at 15 cm. The solution was maintained at 25° C. with a water bath.

At ½ hour the above solution was poured into ½ volume of 10% NaHSO₃ (aq.). The aqueous phase was extracted four times with equal volumes of CH₂Cl₂. The combined extracts were dried over Na₂SO₄, filtered, and reduced in vacuo. Crude mass balance was approximately 100%. The crude 9-alpha-chloro compound 13 contained about 10% unreacted starting material.

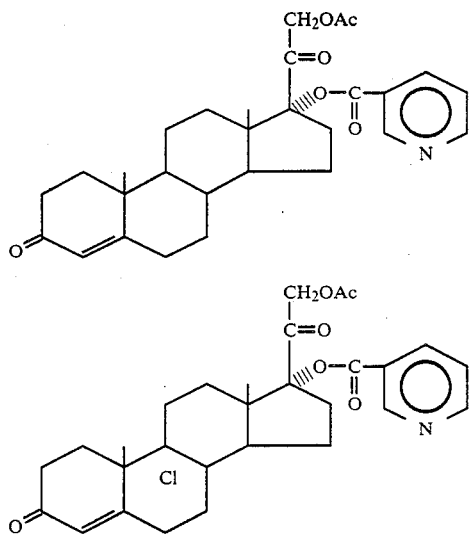

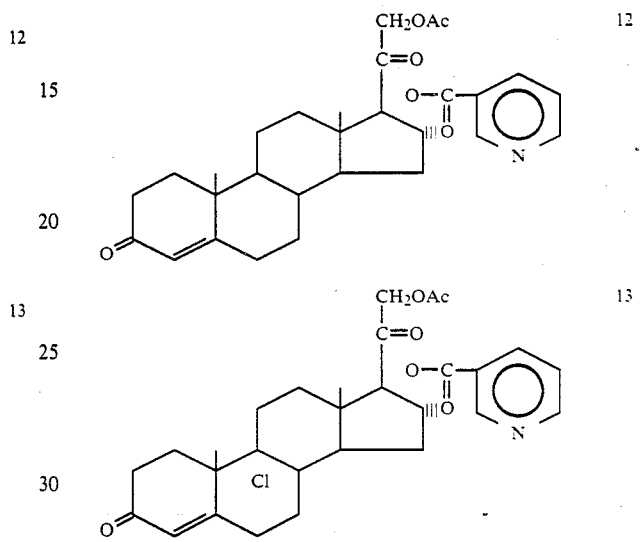

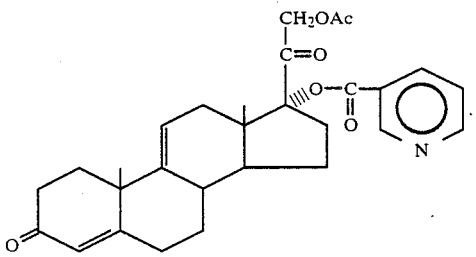

EXAMPLE 6

The 9-alpha-chloride 13, as obtained from the chlorination reaction without purification, (0.21 mmol. assumed, 1.0 equiv.) was dissolved in 3 ml acetone. Solid AgBF (55 mg., 0.28 mmol., 1.3 equiv.) was added. The solution was stirred 12 hrs. The resulting suspension was diluted with NH₄Cl (sat'd aq.) and CH₂Cl₂. The phases were separated, and the aqueous phase was extracted five times with CH₂Cl₂. The combined extracts were dried over Na₂SO₄, filtered, and reduced in vacuo. Material recovery was approximately 100%.

Chromatography on SiO₂ with CH₂Cl₂:acetone (8:1) was performed. The pure Δ4,9(11) diene 14 is recovered in 70% yield. (Material recovery from the column was equal to or less than 80%.)

EXAMPLE 8

291 mg. of cortexolone-21-acetate, 941 mg. of nicotinic anhydride, and 869 mg. of 4-dimethylaminopyridine were suspended in 7 ml. of 1,2-dimethoxyethane. The mixture was heated at 55° C. for 31 hours, then quench with aqueous ammonium chloride (NH₄Cl) and extracted with methylene chloride.

Chromatography on silica (SiO₂) afforded 358 mg. (97% yield) of the product ester 12 as a glass and a small amount of recovered starting material. NMR and mass spectrum of the product confirmed structure 12.

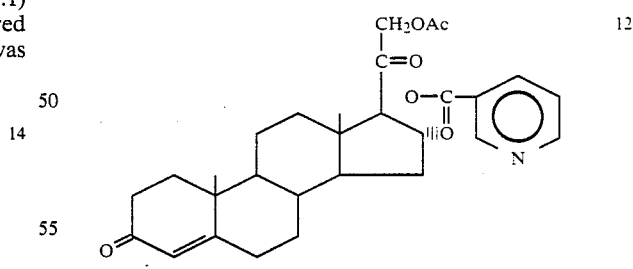

EXAMPLE 7

The 17-alpha-nicotinate 12 (15 mg., 0.03 mmol., 1.0 equiv.) was dissolved in 10 ml. CH₂Cl₂. Azobisisobutyronitrile (1 mg., 0.006 mmol., 0.2 equiv.) was added, followed by sulfuryl chloride (5 μl., 0.06 mmol., 2.0 equiv.). The mixture was irradiated with a 275 W sun-

What is claimed is:

1. A method of substituting a chlorine atom for a predetermined hydrogen atom attached at the carbon-6, -9, -14, -17, or -20 position of a steroid, which steroid is selected from the group consisting of steroids of the cholestane, androstane, and pregnane series and has a hydroxyl group, comprising (a) reacting the steroid with an esterifying agent under suitable conditions so as to produce an ester, the esterifying agent comprising a pyridine ring or a substituted or fused ring derivative of a pyridine ring; and (b) treating the resulting ester with a chlorinating agent in an organic solvent under conditions such that the chlorine atom is substituted for the predetermined hydrogen atom.

2. A method of claim 1, wherein the steroid is a steroid of the cholestane series and wherein the Hydroxyl group is located at the 3-alpha position.

3. A method of claim 2, wherein the esterifying agent comprises a nicotinate or isonicotinate moiety or substituted derivative thereof and the ester is a 3-alph-cholestanyl nicotinate or 3-alpha-cholestanyl isonicotinate.

4. A method of claim 1, wherein the steroid is a steroid of the pregnane series and wherein the hydroxyl group is located at the 17-alpha position.

5. A method of claim 4, wherein the steroid of the pregnane series further contains a methyl group attached at carbon-16.

6. A method of claim 5, wherein the methyl group is in the alpha position.

7. A method of claim 1, wherein the steroid is cortexolone or a substituted derivative thereof.

8. A method of claim 7, wherein the cortexolone or substituted derivative thereof further comprises a methyl group attached at carbon-16.

9. A method of claim 8, wherein the methyl is in the alpha position.

10. A method of claim 9, wherein the esterifying agent comprises a nicotinate or isonicotinate moiety of substituted derivative thereof and the ester is a 16-alpha-methylcortexolone-17-alpha-nicotinate or 16-alpha mehtylcortexolone-17-alpha-isonicotinate.

11. A method of claim 7, wherein the esterifying agent comprises a nicotinate or isonicotinate moiety or substituted derivative thereof and the ester is a 17-alpha cortenolone nicotinate or 17-alpha-cortexolone isonicotinate.

12. A method of claim 1, wherein the predetermined hydrogen is attached to carbon -9.

13. The method of claim 1, wherein the predetermined hydrogen is attached to carbon -14.

14. A method of claim 1, wherein the esterifying agent comprises a nicotinate or isonicotinate moiety or substituted derivative thereof.

15. A method of claim 14, wherein the steroid is contacted with the esterifying agent so as to produce the ester at the 3-alpha or 17-alpha position of the steroid.

16. A method of claim 1, wherein the chlorinating agent is molecular chlorine, phenyliododichloride, or sulfuryl chloride.

17. A method of claim 16, wherein the chorinating agent is phenyliododichloride or sulfurylchloride.

18. A method of claim 1, wherein the treating comprises irradiating the organic solvent containing the resulting ester and the chlorinating agent.

19. A compound having the structure:

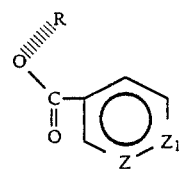

wherein R is a steroid moiety of the cholestane, androstane or pregnane series and either Z or $Z_1$ is a nitrogen atom and the other is a carbon atom.

20. A compound of claim 19 further comprising a chlorine atom attached to the nitrogen atom of the pyridine ring.

21. A compound of claim 19, wherein the group having the structure:

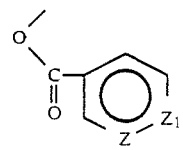

is attached to R at the 3-alpha or 17-alpha position.

22. A compound of claim 21, wherein R is a cholesterol, cortexolone, or methylcortexolone moiety or substituted derivative thereof.

23. A compound having the structure:

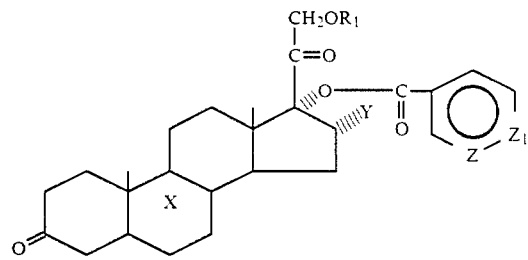

wherein either Z or $Z_1$ is a nitrogen atom and the other is a carbon atom; X is a hydrogen or chlorine atom; Y is a hydrogen atom or a methyl group; $R_1$ is a hydrogen atom or an acetate group; and the dotted lines (....) represent bonds which may be present or absent.

24. A compound having the structure:

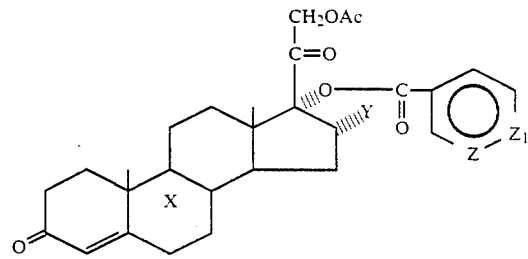

wherein either Z or $Z_1$ is a nitrogen atom and the other is a carbon atom; X is a hydrogen or chlorine atom; and Y is a hydrogen atom or a methyl group.

* * * * *